United States Patent [19]

Ohsugi et al.

[11] 4,106,988

[45] Aug. 15, 1978

[54] METHOD OF CULTIVATING *METHYLOMONAS PROBUS* ON METHANOL CONTAINING MEDIUM

[75] Inventors: Katsuhisa Ohsugi; Daizo Takeuchi; Masahiro Hamada; Tamotsu Kano, all of Iwaki, Japan

[73] Assignee: Kureha Kagaku Kogyo Kabushiki Kaisha, Tokyo, Japan

[21] Appl. No.: 770,655

[22] Filed: Feb. 22, 1977

[51] Int. Cl.$^2$ .............................................. C12B 1/00
[52] U.S. Cl. ........................................ 195/49; 195/96; 426/656; 426/807
[58] Field of Search ................... 195/96, 49; 426/807, 426/656

[56] References Cited

U.S. PATENT DOCUMENTS

| 3,989,594 | 11/1976 | MacLennan et al. | 195/49 |
| 3,994,781 | 11/1976 | Thorstendotter | 195/49 |

FOREIGN PATENT DOCUMENTS

| 7,372,382 | 9/1973 | Japan | 195/49 |
| 103,795 | 12/1973 | Japan | 195/49 |
| 7,581,874 | 7/1975 | Japan | 195/49 |

*Primary Examiner*—Raymond N. Jones
*Assistant Examiner*—Thomas G. Wiseman
*Attorney, Agent, or Firm*—Lane, Aitken, Dunner & Ziems

[57] ABSTRACT

A new species of bacteria, *Methylomonas probus*, is cultured in a medium containing methanol as a sole carbon source to obtain propagated bacterial cells that can be utilized as an effective source of protein in feed and food.

5 Claims, No Drawings

METHOD OF CULTIVATING *METHYLOMONAS PROBUS* ON METHANOL CONTAINING MEDIUM

FIELD OF THE INVENTION

This invention relates to a method of producing microbial cells usable as a source of protein for feed and food, and more particularly to a method of producing the cells of a new species of bacteria, *Methylomonos probus*, for such purpose.

BACKGROUND OF THE INVENTION

If the population of the world continues to increase at the present rate of 76,000,000, persons a year as U.N. statistics show, it is quite probable that the mankind will confront a serious food crisis even within this century as the prospects for food supply in the future are very bleak.

Efforts for increasing the sources of protein in the fields of agriculture and fisheries are subject to certain restrictions as it is hardly possible to drastically expand the acreage of agricultural cultivation or the fishing grounds and also because the yields of agricultural and marine products are greatly affected by weather and, further, a drop yield is unavoidable in future cultivation as the area for such cultivation is being cornered into an unfavorable environment due to steady expansion of population and industrial areas. Under such circumstances, high hopes are placed on utilization of single cell protein which can be produced in commercial quantity and with high efficiency in all seasons of the year without being affected by weather and also without causing natural environmental disruptions.

Heretofore, saccharides, sulfite pulp waste liquor and such have been used as base materials for producing microbial cells such as yeast cells, and interest has been aroused recently in normal paraffin which can be obtained from petroleum fractions at relatively low cost, and efforts are being made in many countries for producing the microbial cells using such normal paraffin as a carbon source to produce so-called petroleum protein. However, use of such normal paraffin as a base material for production of microbial cells also involves many difficult problems such as listed below.

(1) Since normal paraffin is almost insoluble in the culture medium, means for facilitating its culture, such as high speed agitation, addition of emulsifying or dispersing agents, large-scale aeration, etc., are required, resulting in increased consumption of energy.

(2) As much heat energy for fermentation is generated, high cooling cost is encountered.

(3) High refining cost is required for removing harmful substances such as 3,4-benzpyrene.

(4) It is not easy to remove normal paraffin from the produced microbial cells.

In an attempt to overcome such problems, use of acetic acid, ethanol, waste materials from processing of agricultural and marine products and the like as base material (carbon source) for production of microbial cells has been proposed. However, these materials still have many difficultires with regard to cost and stable supply. Methane and carbon dioxide are also noticed with interest for use as the base material because they can be supplied in abundance at low cost, but use of these materials is attended by the problems that growth rate of the microorganisms is unsatisfactory and that cost for production equipment is high because these materials are gaseous form.

In view of the foregoing, we have studied carbon sources for production of microbial cells and reached the conclusion that methanol is free of the difficulties such as mentioned above and therefore best suited for use as the carbon source. Methanol can be produced in commercial quantity from petroleum, coal and natural gas, so that its supply is stable and it is also obtainable at relatively low cost. Further, as methanol is soluble in water, it is suited for use as carbon source in the culture medium of microorganisms.

We then pursued a search for microorganisms which are effectively capable of assimilating methanol as a carbon source.

Mold, yeast and bacteria are known as typical examples of microorganisms which are capable of assimilating methanol as a sole carbon source. However, mold and yeast are lower in growth rate than bacteria, and also yeast requires expensive growth factors, so that these substances are disadvantageous for producing the preferred microbial cells economically. It is to be also noted that both mold and yeast are lower in crude protein content, which is an important factor in determining the nutritive qualities of the microbial cells, and also lower in sulfur-containing amino acid content in cell protein than bacteria.

Yeast has been considered advantageous because of its lower nucleic acid content than bacteria, but the protein to nucleic acid content ratio of yeast is substantially equal to that of bacteria. Thus, it may be said that it is most advantageous for improving productivity to use protein-rich bacterial cells as a protein source in feed and food.

Many reports have been published recently on the types of bacteria that can propagate microbial cells by utilizing methanol as a carbon source. Representative of such reports are the following: Preparation of Cells by Use of Bacteria Belonging to Pseudomonas by Kono et al. (Collection of Summaries of Lectures at Japan Agricultural Chemistry Society Congress 1H-23, 1970), Production of Cells by Use of *Achromobacter methanolophia* and *Pseudomonas insneta* by Kurasawa et al (Collection of Summaries of Lectures at Japan Agricultural Chemistry Society Congress 4I-31, 1970), and Production of Cells Using *Pseudomonas methanolica* by Terui et al (Collection of Summaries of Lectures at Japane Agricultural Chemistry Society Congress 2E-07, 1971).

Our search for bacteria that can provide useful microbial cells by utilizing methanol succeeded in isolating a new species of bacteria which allows most effective utilization of methanol and which has an extremely high growth rate and also high cell protein. On the basis of this success, we formulated the present invention which provides a method of producing microbial cells that can be utilized as a high-quality protein source by culture the new species of bacteria in a medium containing methanol as the carbon source.

SUMMARY OF THE INVENTION

This invention relates to a method of production the microbial cells from a new species of bacteria, *Methylomonas probus*, by culture and propagating it in a medium containing methanol as carbon source.

The microbes used in this invention has many differences from any of the known bacteria, so that it was judged as a new species of bacteria and named *Methylomonas probus* NB-2000. This new bacterium was deposited under deposition No. FERM-P No. 3193, on August 14, 1975, in the Fermentation Research Institute of Agency, Industrial Science and Technology (Chiba-shi, Japan), a government agency designated by the Director-General of the Patent Office of Japan.

This invention is aimed at providing a method of advantageously producing the protein-rich microbial cells which can be beneficially utilized as a source of protein in food. The other objects of this invention will become apparent from reviewing the following detailed description of the invention.

DETAILED DESCRIPTION OF THE INVENTION

The method of this invention comprises the steps of culturing and propagating *Methylomonas probus* in a medium containing inorganic nutrients and methanol as a carbon source, and then separating and collecting the propagated microbial cells.

*Methylomonas probus* used in this invention has the following mycological properties.

a. Morphological properties

| (1) Shape and size of cells: | A single or 2 to 3 chain bacillus with a size of 0.5–0.7 × 1.0–1.5μ. |
|---|---|
| (2) Polymorphism of cells: | Has no polymorphism. |
| (3) Mobility: | Has mobility with single polar flagellum. |
| (4) Spore: | Non-sporiferous. |
| (5) Gram stainning: | Gram negative. |

Examination of the above morphological properties was made on the cells which were cultured in an inorganic salt synthetic medium (1) (the composition of the medium being shown later) at 30° C for 24 to 48 hours.

| (6) Acid fastness: | − (minus) |
|---|---| b. Condition of growth in culture media (1) Agar plate culture with inorganic salt synthetic medium (1):

The bacterium of this invention grows abundant and forms smooth, entire and convex circular colonies. The colonies are semi-transparent and have luster. The color is grayish white or pink.

(2) Agar slant culture with inorganic salt synthetic medium (1):

Growth of the bacterium is of a medium degree. The formed colony is filiform and has luster. The color is grayish white or pink. No diffusive pigment is produced.

(3) Bouillon agar plate culture:

No growth or only a very slight degree of growth takes place. Where a slight degree of growth takes place, the formed colony is less than 0.5 mm in size (in 48-hour cultivation at 30° C). It is smooth circular, lustrous and transparent.

(4) Bouillon agar slant culture:

No growth or only a slight degree of growth is seen. In the latter case, the formed colony is filiform and transparent.

(5) Bouillon liquid culture:
No growth is noticed.

(6) Bouillon gelatin stab culture:
No growth is noticed, and gelatin is not liquefied.

(7) Litmus milk (litmus mild specimens mfd. by Difco Inc.):

No change occurs. Addition of 1% of methanol causes no change, either.

c. Various physiological properties

As no sufficient growth is produced in the mediums below by the normal method, each of the following tests (1) to (8), was conducted by using a traditional medium supplemented with 1% of methanol.

| | | |
|---|---|---|
| (1) Nitrate reductivity: | | + |
| (2) Denitrification reaction | | − |
| (3) VP test | | − |
| (4) MR test | | − |
| (5) Indole formability | | − |
| (6) Formation of hydrogen sulfide | | − |
| (7) Starch hydrolyzability | | − |
| (8) Utilization of citric acid | | − |
| (9) Formation of pigment: | | No color pigment is produced in King culture media A or B. A small amount of water-soluble yellow pigment is released when using an inorganic salt synthetic liquid medium. Produced bacterial cells are grayish pink. |
| (10) Utilization of nitrogen sources: | | Ammonium chloride, ammonium sulfate, primary ammonium phosphate, secondary ammonium phosphate, urea, ammonium nitrate, ammonium carbonate and polypeptone are well utilized as nitrogen sources in inorganic nutritive solutions. Nitrate, nitrite, methylamine, casamino acid and yeast extract are also utilized, but the degree of utilization of these substances is relatively low. |
| (11) Urease | | + |
| (12) Oxidase | | + |
| (13) Catalase | | + |
| (14) Range of growth conditions: | | PH: 5.3–9.1; optimum PH range: 6.3–7.0. Temperature: 15–41° C; optimum temperature range: 35–37° C. |
| (15) Attitude to oxygen: | | Aerobic. |
| (16) O-F test (by Hugh-Leifson method): | | No generation of gas and acid is noticed. |
| (17) Utilization of para-hydroxybenzoate: | | − |
| (18) Ammonia formability | | − |
| (19) Sugar fermentability: | | Each of the hereinbelow listed sugars has no fermentability. (Results of 30-day observation of peptone solution, containing 1% of each sugar). L-arabinose D-xylose D-glucose D-mannose D-fruetose D-galactose Maltose Sucrose Lactose Trehalose L-rhamnose Mannitol Sorbitol Glycerin Starch |
| (20) Utilization of various carbon sources: | | |
| Methanol | 0.5 | + |
| Ethanol | 0.5 | − |
| n-propanol | 0.5 | − |
| iso-propanol | 0.5 | − |
| n-butanol | 0.5 | − |
| Sodium formate | 0.01 | − |
| Formaldehyde | 0.01 | − |
| Sodium acetate | 0.5 | − |
| Sodium lactate | 0.5 | − |
| Sodium succinate | 0.5 | − |
| Sodium pyruvate | 0.5 | − |
| Monomethylamine | 0.5 | + |
| Methane (aerated with 1 : 1 air-methane mixture gas) | | − |

-continued

| | | |
|---|---|---|
| n-tetradecane | 0.5 | — |
| n-hexadecane | 0.5 | — |
| n-octadecane | 0.5 | — |
| Arabinose | 0.5 | — |
| Glucose | 0.5 | — |
| Fructose | 0.5 | — |
| Galactose | 0.5 | — |
| Maltose | 0.5 | — |
| Sucrose | 0.5 | — |
| Lactose | 0.5 | — |
| Rhamnose | 0.5 | — |
| Mannitol | 0.5 | — |
| Sorbitol | 0.5 | — |
| Starch | 0.5 | — |
| Sodium alginate | 0.3 | — |
| Phenol | 0.01 | — |
| Peptone | 0.5 | — |
| Casamino acid | 0.5 | — |
| Yeast extract | 0.5 | — |
| Indole | 0.5 | — |
| Nutrient broth | 0.5 | — |

(Note)
Each of the above listed substances was added in the amount indicated to the inorganic salt synthetic medium (1) of the following composition from which methyl alcohol was excluded, and the growth of the bacterium was observed for a period of 30 days. The substances which produced a noticeable degree of growth of the bacterium are indicated with + mark.

| (Composition of inorganic salt synthetic medium (1) | |
|---|---|
| $(NH_4)_2HPO_4$ | 3.5 g |
| $KH_2PO_4$ | 1.5 g |
| $K_2HPO_4$ | 1.5 g |
| $MgSO_4 \cdot 7H_2O$ | 0.3 g |
| $CaCl_2 \cdot 2H_2O$ | 0.01 g |
| $FeSO_4 \cdot 7H_2O$ | 0.01 g |
| Methanol | 2% (V/V) |
| Service water | 1 litre |

By checking the above-described bacteriological properties with reference to "Bergey's Manual of Determinative Bacteriology Vol. 8", it was confirmed that the bacterium of this invention belongs to the *Methylomonas* genus. According to the same manual, there exist three species of *Methylomonas* bacteria, namely, *Methylomonas methanica, Methylomonas methanoloxidans* and *Methylomonas methanitrificans*, but judging from the various properties such as mentioned above, the bacterium of this invention is not any of these species. The bacterium of this invention is distinguishable from the other known analogous methanol-utilizing protein-providing bacteria in the following particulars.

The bacterium of this invention (hereinafter referred to as the present bacterium) differs from *Pseudomonas utilis* (disclosed in Japanese Patent Laid-Open No. 93589/1974) in growing temperature and optimum growing temperature as well as in urease (−) and pigment formation (−)

Also, the present bacterium differs from Pseudomonas inaudita (disclosed in Japanese Pat. Laid-Open No. 93589/1974) in optimum growing temperature by as much as 2° to 10° C and is also different in pigment formation (−) and utilization of para-hydroxybenzoate. The present bacterium is also different from Methylomonas methanolica nov. SP. (reported by Terui et al in Journal of Fermentation Technology, Vol, 53, page 315, 1975) in temperature growth, optimum growing temperature, pH growth range, colony color tone and ability to turn monomethylamine into a useful nitritive source.

Further, the present bacterium is distinguishable from *Methylomonas methanolica* (disclosed in Japanese Pa. Laid-Open No. 103795/1973) in color tone of the colony on the inorganic salt synthetic medium and also in that the present bacterium grows briskly even in 40° C secondary culture and that the optimum growing temperature is 5° to 7° C higher that that for said known bacterium. The fact that the optimum growing temperature for the present bacterium is as much as 5° to 7° C higher than that for the known bacterium is acknowledged as a very significnt difference both microbiologically and from the viewpoint of cooling efficiency in production of bacterial cells.

The present bacterium is also different from those reported by Whittenbury et al (J. Gen. Microbiol, 61, 205, 1970) such as *Methylomonas albus, Methylomonas methanica, Methylomonas agile* and *Methylomonas rubrun*, because all of these bacteria assimilate methane and also their maximum specific growth rate ($\mu$ max) with methanol is on the order of 0.17 to 0.23 $hr^{-1}$, whereas the present bacterium is incapable of assimilating methane and $\mu$ max with mathanol is 0.82 $hr^{-1}$, or more than twice as high as that of the known bacteria.

For these reasons, it may rightly be concluded that the bacterium used in this invention is a new species of Methylomonas bacteria.

The medium used for culture the new species of bacterium in this invention may be any type of aqueous medium commonly employed for growing of bacteria, provided that methanol is used as a carbon source. The medium may contain nitrogen and inorganic nutrient sources in addition to the carbon source.

The methanol concentration in the medium may span a wide range from a low concentration level to a high level of around 4% for retaining satisfactory growth rate of the bacterium. However, the growth rate of the bacterium decreases gradually as the methanol concentration exceeds 4%. Since the methanol concentration in the medium decreases with advance of cultivation of the bacterium, methanol may be supplied to the medium at need during the period of cultivation.

Culture and propagation of the bacterial cells according to this invention is practiced under aerated aerobic conditions with a pH of 5.3 to 9.1, preferably 6.3 to 7.0, and at a temperature of 15° to 41° C, preferably 35° to 37° C. A preferred amount of bacterial cells can be obtained in approximately 48 hours after start of cultivation. The yield is elevated if the aeration rate is increased with time during cultivation. As a high cultivation temperature, 41° C at highest, can be applied in the process of this invention, a higher cooling efficiency is provided in production of the bacterial cells as compared with the other known mehods of this type.

The crude protein content in the bacterial cells obtained according to the method of this invention may reach as high as 80%, and as clarified in the following description of this invention, such bacterial cells are of high nutritive value and also non-toxic, so that they provide an excellent protein source when mixed in feed and food.

The present invention is now described in further detail by way of several embodiments, but as obvious, the scope of this invention is not limited to these embodiments.

EXAMPLE I 3.0 gr of $(NH_4)_2HPO_4$, 1.5 gr of $KH_2PO_4$, 1.5 gr of $K_2HPO_4$, 0.5 gr of $MgSO_4.7H_2O$ and 0.1 gr of $FeSO_4.7H_2O$ were dissolved in 1 liter of ion exchange water to prepare a solution (pH: 7.0), and each 100 ml of this solution was placed in a 300 ml capacity conical flask, and after sterilization, 1.6 gr of methanol was added to the solution in each of said flasks to thereby prepare culture media. Then each of the thus prepared media was inoculated with *Methylomonas probus* FERM-P. No. 3193 (cultivated in an agar slant culture medium of the same composition as mentioned above) and subjected to 2-day shaking culture at 30° C. After culture, the bacterial cells were collected by a centrifugal separator, washed with deionized water and dried at 110° C until a constant weight was reached. There was consequently obtained 7.2 gr of dry cells per 1 liter of the culture solution, representing a yield of 45.0% based on the methanol added.

EXAMPLE II

A culture medium was prepared by introducing 200 ml of methanol (1.0% (V/V) into a 30-liter-capacity jar fermentor contaning 20 liters of a solution (pH: 7.0) prepared by dissolving 4.0 gr of $(NH_4)_2HPO_4$, 1.0 gr of $KH_2PO_4$, 1.0 gr of $K_2HPO_4$, 0.5 gr of $MgSO_4 \cdot 7H_2O$ and 0.1 gr of $FeSO_4 \cdot 7H_2O$ in 1 liter of deionized water, and sterilizing and this medium was inoculated with 2% (V/V) of *Methylomonas probus* FERM-P No. 3193 which had been cultured in an identical medium, and cultivated at 35° C under agitation at the rate of 500 rpm and aerated at the rate of 30 1/20 l/min (1.5 v.v.m.). Cultivation was continued for 48 hours by increasing the aeration rate gradually from the above-said rate to 40 1/20 l/min (2.0 v.v.m.), then to 50 1/20 l/min (2.5 v.v.m.) and then further to 60 1/20 /min (3.0 v.v.m.). During culture, the pH was automatically controlled at 6.6 to 7.2 with 14% ammonia water, and methanol was supplied automatically such that it would be consumed at the rate of 0.3 to 1.0% as measured by gas chromatography.

After culture, the produced bacterial cells were collected by centrifugal separation, washed with deionized water and dried at 110° C until a constant weight was reached. Consequently, dry bacterial cells were obtained in yields of 2.50 g/l after 28 hours of culture, 40.7 g/l after 40 hours, and 53.8 g/l after 48 hours.

EXAMPLE III

The following substances:

| | | | |
|---|---|---|---|
| $(NH_4)_2HPO_4$ | 4 g | $(NH_4)_2SO_4$ | 0.8 g |
| $KH_2 \cdot PO_4$ | 1.0 g | $K_2HPO_4$ | 1.0 g |
| $MgSO_4 \cdot 7H_2O$ | 0.7 g | $FeSO_4 \cdot 7H_2O$ | 0.1 g |
| $MnSO_4 \cdot 4-6H_2O$ | 0.01 g | $ZnSO_4 \cdot 7H_2O$ | 0.01 g |
| $CuSO_4 \cdot 5H_2O$ | 0.01 g | $CaCl_2 \cdot 2H_2O$ | 0.01 g |
| $CoCl_2 \cdot 6H_2O$ | 0.01 g | $(NH_4)_6Mo_7O_{24} \cdot 4H_2O$ | 0.01 g | were dissolved, each in the above-specified amount, in deionized water to prepare a 1-liter mixture. Then 20 liters of this mixed solution was put into a 30-liter-capacity jar fermentor and, after 15-minute sterilization at 120° C, methanol was added in concentration of 2% (V/V) to thereby prepare a culture medium. This medium was then inoculated with a culture solution of *Methylomonas probus* FERM-P No. 3193 (which had been cultivated 18-hour with shaking in the same medium as above (methanol content: 1.0% (V/V)) at the rate of 2% (V/V) and cultivated for 28-hours at 37° C under agitation at 500 rpm and aeration of 30 1/20 l/min (1.5 v.v.m.) while automatically maintaining pH of the medium at 6.6 to 7.2 by using 14% ammonia water.

As methanol is consumed with growth of the bacterium, the methanol concentration in the culture solution was measured by gas chromatography and methanol was added continuously by a micro constant-delivery pump such that the methanol concentration remained at 0.3 to 2.0% (V/V) during culture. A total amount of 1,035 gr of methanol was added during cultivation.

The produced bacterial cells were collected by centrifugal separation and, after washing with deionized water, dried at 110° C until a constant weight was reached. There was consequently obtained 25.6 gr of dry cells per 1 liter of culture solution, representing a yield of 49.5% as calculated on the basis of methanol added.

The crude protein content was 80.3% (N% × 6.25).

The growth rate of the bacterium was determined by measuring turbidity of the culture solution by a colorimeter (610 m$\mu$). The maximum specific growth rate was as high as 0.82 hr$^{-1}$ and generation time was as short as 51 minutes.

EXAMPLE IV

The bacterium of the same strain as used in the preceding examples was subjected to batch culture under the same conditions as employed in Example III. As the dissolved oxygen concentration in the culture solution dropped with growth of the cells, the medium aeration rate was raised to 40 1/20 l/min (2.0 v.v.m.), then to 50 1/20 l/min (2.5 v.v.m.) and then to 60 1/20 l/min (3.0 v.v.m.) successively, and at a point where the cell concentration (X g/l) in the cultivation solution reached 43.6 g/l, batch culture was switched to continuous cultivation by continuously feeding the same medium as used in batch culture into the cultivation solution at the dilution rate (D:hr$^{-1}$) of 0.28 hr$^{-1}$ while simultaneously drawing out an equal quantity of the culture solution from the jar fermentor. PH of the medium was automatically controlled to stay within the range of 6.6 to 7.2 by using 14% ammonia water, and the methanol consumed with advance of the bacterial cell production was automatically supplied such that the methanol concentration in the culture solution would always remain within the range of 0.3 to 1.0% (V/V) as measured by gas chromatography. Continuous cultivation was carried on at an extremely high productivity of D·X = 8.1 g/l. hr throughout the process.

The following Examples V to X show the relationship between aeration rate and cell productivity in culture according to the method of this invention.

EXAMPLE V

The bacterium of the same strain as used in Example III was cultured under the same conditions as employed in said example. Continuous cultivation at an aeration rate of 30 1/20 l/min (1.5 v.v.m.) provided productivity of 4.2 g/l. hr.

EXAMPLE VI

Cultivation was carried out by using the same strain of bacterium and under the same conditions as used in Example III continuously at an aeration rate of 40 1/20 l/min (2.0 v.v.m.). Productivity was 5.6 g/l. hr.

EXAMPLE VII

Cultivation was carried out in the same way as Example III continuously at an aeration rate of 50 1/20 l/min (2.5 v.v.m.), obtaining a productivity of 7.3 g/l. hr.

EXAMPLE VIII

Cultivation was carried out after the manner of Example III continuously at aeration rate of 60 1/20 l/min (3.0 v.v.m.), obtaining a productivity of 8.1 g/l.hr.

EXAMPLE IX

Continuous cultivation was carried out at aeration rate of 80 1/20 1/min (4.0 v.v.m.) by using the same strain of bacterium and under the same conditions as employed in Example III, obtaining a productivity of 9.3 g/l. hr.

EXAMPLE X

Continuous cultivation at aeration rate of 100 1/20 1/min (5 v.v.m.) was conducted in the same way as Example III, obtaining a surprisingly high productivity of 12.2 g/l.hr.

EXAMPLE XI

Male rat feeding test using the *Methylomonas probus* FERM-P No. 3193 cells obtained by the above-mentioned methods:

A feeding test was conducted on 60 Wistar rate (3 weeks old) by using experimental diets of the following composition as base feed.

| Vitamin-free casein | 12.0% | Corn starch | 61.0% |
|---|---|---|---|
| Sugar | 5.0% | Cellulose powder | 11.5% |
| Soy bean oil | 6.0% | Vitamin A and D | 0.2% |
| Vitamin B group | 0.3% | Minerals | 4.0% |
| $Na_2SeO_3$ | 0.2 ppm | | |

After feeding the rats with the base feed for 5 days, they were divided into three groups of 20. The rats of the first group were given the base feed continuously as a control group, while the other two groups were designated test group I and test group II, respectively, and the rats of test group I were given the base feed from which vitamin-free casein (12.0%) was removed and to which 20% of dry bacterial cells of this invention was added, while the rats of test group II were given the base feed from which vitamin-free casein (6.0%) was removed and to which 10% of dry bacterial cells was added.

The rats of these three groups were fed with the above-mentioned respective feeds for 5 weeks, and the body weights and feed intakes of the rats of the respective groups during this period were measured. The results are shown in Table 1 below.

Table 1

| | | Body weight | | Feed | |
|---|---|---|---|---|---|
| | Average at start | Average after 5 weeks | Average body weight increment | Average feed intake | Average feed demand |
| Control | $59.9 \pm 3.0^{(g)}$ | $175.2 \pm 16.6^{(g)}$ | $115.3 \pm 17.0^{(g)}$ | 484.8 | $4.20 \pm 0.41$ |
| Test group I | $60.1 \pm 3.1$ | $175.5 \pm 1.45$ | $115.4 \pm 14.9$ | 466.1 | $4.04 \pm 0.34$ |
| Test group II | $59.8 \pm 3.0$ | $176.3 \pm 15.5$ | $116.5 \pm 15.4$ | 467.2 | $4.01 \pm 0.31$ |

Comparing the rats of test groups I and II with those of the control group, there was observed no difference at all in body weight increment, feed intake and feed demand or in external appearance and mobility such as hair gloss and vivacity. Also, post-test dissective examinations of the internal organs showed absolutely no abnormality. Thus, excellent adaptability of the microbial cells of this invention as protein source for feed was demonstrated.

What is claimed is:

1. A method of producing microbial cells usable as protein source, which comprises cultivating the bacterium Methylomonas probus aerobically in a medium containing methanol as a carbon source, nitrogen and inorganic nutrient sources, and separating, then collecting the thus propagated microbial cells of said bacterium.

2. A method according to claim 1, wherein said cultivation is carried out with aeration at a temperature of 35° to 37° C while controlling pH of the culture solution at 6.3 to 7.0.

3. A method according to claim 1, wherein the methanol concentration in said medium is not higher than 4% by volume.

4. A method according to claim 2, wherein the rate of said aeration is elevated gradually to 40 1/20 1/min, then to 50 1/20 1/mm per minute and then to 60 1/20 1/min.

5. A method according to claim 2, wherein said aeration is carried out at a steady rate in the range of from 10 1/20 1/min to 100 1/20 1/min.

* * * * *

UNITED STATES PATENT AND TRADEMARK OFFICE
CERTIFICATE OF CORRECTION

PATENT NO. : 4,106,988
DATED : August 15, 1978
INVENTOR(S) : Ohsugi et al

It is certified that error appears in the above-identified patent and that said Letters Patent are hereby corrected as shown below:

Column 2, line 47, change "Japane" to --Japan--;
line 65, change "has" to --have--.

Column 5, line 59, after "growth" insert --range--.

Column 6, line 1, change "that" (first occurrence) to --than--;
line 5, change "significnt" to read --significant--;
line 16, "mathanol" should read --methanol--;
line 48, "mehods" should read --methods--.

Column 7, line 16, change "contaning" to --containing--;
line 38, change "in" to --at--; same line, change "2.50" to read --25.0--;
line 54, after "in" insert --a--;
line 58, change "18-hour" to --18-hours--.

Column 8, line 27, "cultivation" should read --culture--;
line 28, "culture" should read --cultivation--;
line 30, change "culture" to read --cultivation--; same line, change "cultivation" to read --culture--.

UNITED STATES PATENT AND TRADEMARK OFFICE
CERTIFICATE OF CORRECTION

PATENT NO. : 4,106,988

DATED : August 15, 1978

INVENTOR(S) : Ohsugi et al

Page 2 of 2

It is certified that error appears in the above-identified patent and that said Letters Patent are hereby corrected as shown below:

Column 9, lines 26 and 27, change "mentioned" to --described--;
line 28, change "rate" to --rats--.

Column 10, line 43, change "50 1/20 1/mm" to read --50ℓ/20ℓ/min.--.

Signed and Sealed this

Twenty-seventh Day of March 1979

[SEAL]

Attest:

RUTH C. MASON
Attesting Officer

DONALD W. BANNER
Commissioner of Patents and Trademarks